United States Patent
Kamiyama et al.

(10) Patent No.: US 11,925,767 B2
(45) Date of Patent: Mar. 12, 2024

(54) CATHETER AND MANUFACTURING METHOD THEREFOR

(71) Applicant: KANEKA CORPORATION, Osaka (JP)

(72) Inventors: Daichi Kamiyama, Settsu (JP); Naotake Maekubo, Okaya (JP)

(73) Assignee: KANEKA CORPORATION, Osaka (JP)

( * ) Notice: Subject to any disclaimer, the term of this patent is extended or adjusted under 35 U.S.C. 154(b) by 784 days.

(21) Appl. No.: 16/966,837

(22) PCT Filed: Feb. 5, 2019

(86) PCT No.: PCT/JP2019/004001
§ 371 (c)(1),
(2) Date: Jul. 31, 2020

(87) PCT Pub. No.: WO2019/156059
PCT Pub. Date: Aug. 15, 2019

(65) Prior Publication Data
US 2021/0038859 A1    Feb. 11, 2021

(30) Foreign Application Priority Data

Feb. 6, 2018   (JP) ................................ 2018-019459

(51) Int. Cl.
*A61B 18/14*     (2006.01)
*A61M 25/00*     (2006.01)
(Continued)

(52) U.S. Cl.
CPC ..... *A61M 25/0012* (2013.01); *A61B 18/1492* (2013.01); *A61M 25/0136* (2013.01);
(Continued)

(58) Field of Classification Search
CPC ...... A61B 18/1492; A61B 2017/00867; A61B 2017/00862; A61B 18/1467; A61M 2205/0266; A61M 25/0158

See application file for complete search history.

(56) References Cited

U.S. PATENT DOCUMENTS 5,454,809 A * 10/1995 Janssen ............. A61B 18/1206
                                                          606/41
5,462,545 A * 10/1995 Wang ................. A61B 18/1492
                                                          606/41
(Continued)

FOREIGN PATENT DOCUMENTS

JP    2010-63708 A      3/2010
JP    2012176163 A  *   9/2012  ............ A61M 25/00
(Continued)

OTHER PUBLICATIONS

International Search Report for PCT/JP2019/004001 (PCT/ISA/210) dated Apr. 23, 2019.

*Primary Examiner* — Jaymi E Della
(74) *Attorney, Agent, or Firm* — Birch, Stewart, Kolasch & Birch, LLP

(57) ABSTRACT

To provide a catheter having electrodes to be subjected to application of voltages different from each other in polarity. An outer tube member (3) having a lumen (2); a handle provided on a proximal side of the outer tube member (3); a plurality of electrodes (5) provided on the outer tube member (3); conducting wires (6) connected to one or more of the electrodes (5) and disposed in the lumen (2), the conducting wires (6); and an operating wire (7) having a distal end portion fixed to a distal end portion of the outer tube member (3), wherein one of the electrodes (5a) is connected to a conducting wire (6a) at a connection point, which is different from a connecting point, where another electrode (5b) is connected to another conducting wire (6b), in a circumferential direction of the outer tube member (3).

10 Claims, 5 Drawing Sheets

(51) Int. Cl.
  *A61M 25/01* (2006.01)
  *A61B 5/287* (2021.01)
  *A61B 18/00* (2006.01)
  *A61N 1/39* (2006.01)

(52) U.S. Cl.
  CPC ......... *A61M 25/0147* (2013.01); *A61B 5/287* (2021.01); *A61B 2018/00357* (2013.01); *A61B 2018/00577* (2013.01); *A61B 2018/00595* (2013.01); *A61B 2018/00839* (2013.01); *A61B 2018/1467* (2013.01); *A61M 25/0045* (2013.01); *A61N 1/3956* (2013.01)

(56) References Cited

U.S. PATENT DOCUMENTS

| | | | | |
|---|---|---|---|---|
| 5,643,197 | A * | 7/1997 | Brucker | A61M 25/0069 604/164.08 |
| 6,592,570 | B2 * | 7/2003 | Abrams | A61L 31/022 604/525 |
| 2002/0046785 | A1 * | 4/2002 | Abrams | A61L 31/14 148/563 |
| 2004/0015065 | A1 * | 1/2004 | Panescu | A61B 18/1492 606/41 |
| 2006/0270969 | A1 * | 11/2006 | Toyonaga | A61B 18/1492 604/21 |
| 2009/0171273 | A1 * | 7/2009 | Hastings | A61M 25/0144 604/95.04 |
| 2011/0160785 | A1 | 6/2011 | Mori et al. | |
| 2016/0184008 | A1 * | 6/2016 | Papaioannou | A61B 5/6852 606/41 |
| 2018/0344395 | A1 * | 12/2018 | Papaioannou | A61B 5/6852 |
| 2019/0001143 | A1 | 1/2019 | Sasaki | |

FOREIGN PATENT DOCUMENTS

| | | | | |
|---|---|---|---|---|
| JP | 2014-97084 A | | 5/2014 | |
| JP | 2014-97085 A | | 5/2014 | |
| JP | 2017-153633 A | | 9/2017 | |
| WO | WO-2016064763 A1 * | | 4/2016 | A61B 1/0011 |
| WO | WO-2017156039 A1 * | | 9/2017 | A61B 18/1492 |

* cited by examiner

[FIG. 1]
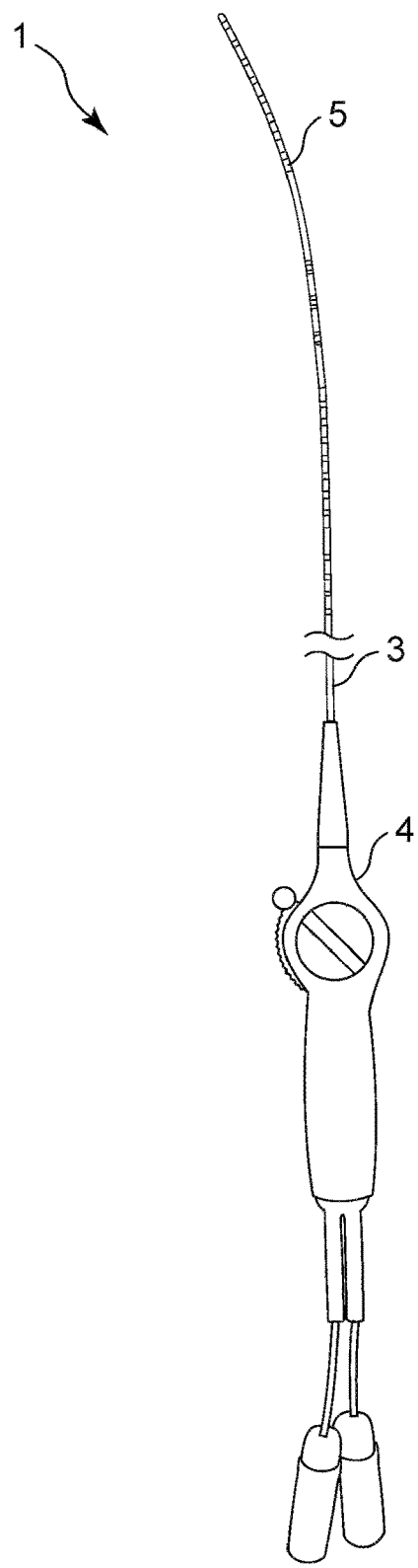

[FIG. 2]
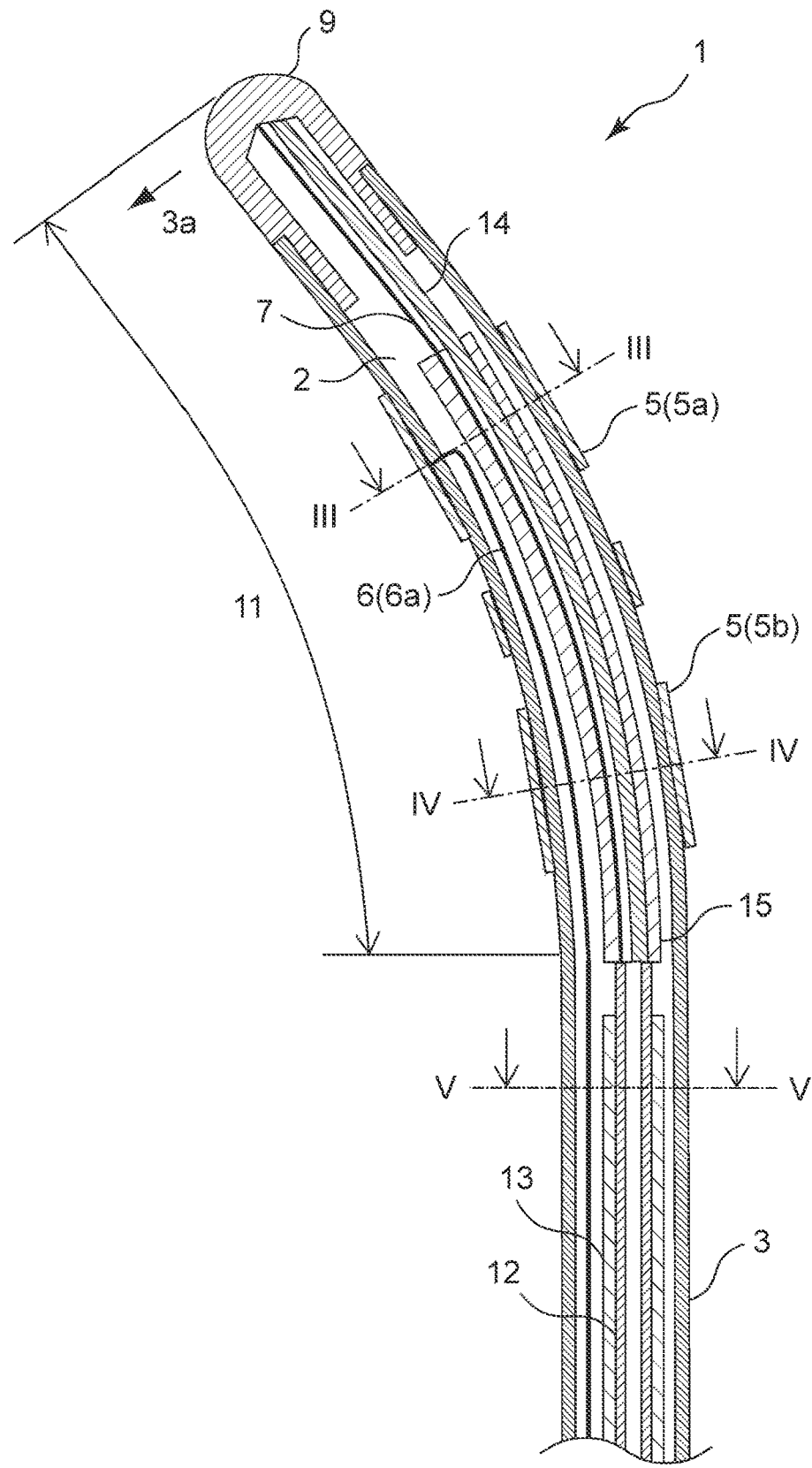

[FIG. 3]
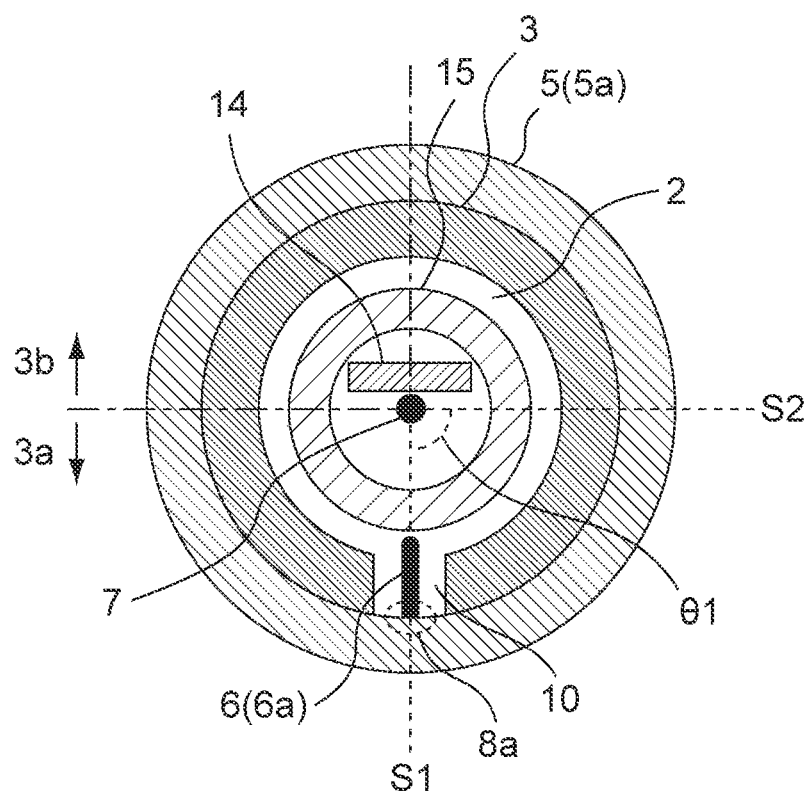

[FIG. 4]
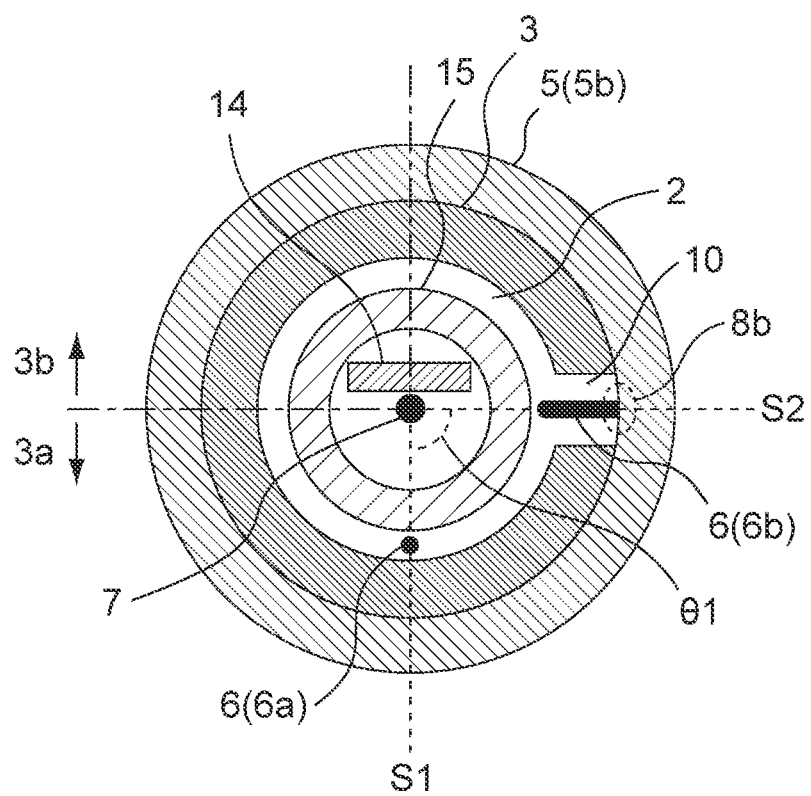

[FIG. 5]
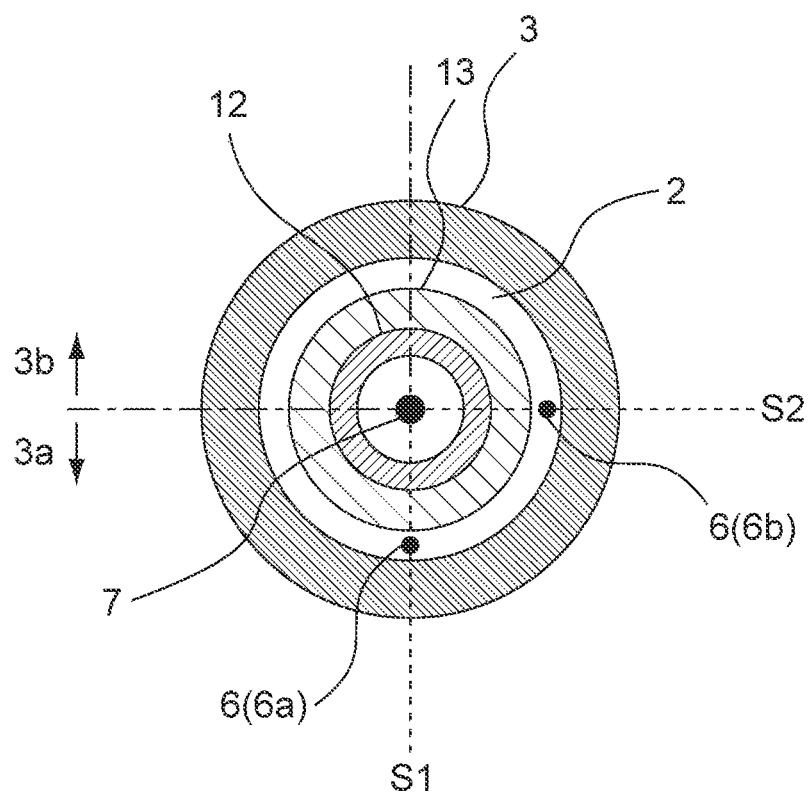

CATHETER AND MANUFACTURING METHOD THEREFOR

TECHNICAL FIELD

The present invention relates to a catheter of which an outer tube member has electrodes.

BACKGROUND ART

In a checkup or a therapy for arrhythmia such as atrial fibrillation, a catheter having electrodes may be used. At the time of the checkup, the catheter is inserted into a heart chamber, where an intracardiac potential is measured to identify an abnormal site in the heart that is the cause of the arrhythmia. At the time of the therapy, high-frequency current is caused to flow from the electrodes of the catheter to a cardiac muscle that is the cause of the arrhythmia, and the source of the arrhythmia is cauterized, thereby electrically ablating the source from the heart (ablation surgery). Meanwhile, if atrial fibrillation naturally occurs or atrial fibrillation is caused for identifying the abnormal site of the heart during the checkup or the therapy, electrical stimulation is applied to the heart from the electrodes of the catheter, to perform defibrillation.

As such a catheter, a catheter is known which includes: an insulating tube member having a multi-lumen structure; a first electrode group composed of a plurality of ring-shaped electrodes mounted in a distal end region of the tube member; a second electrode group composed of a plurality of ring-shaped electrodes mounted in the distal end region of the tube member so as to be apart from the first electrode group to a proximal end side; a first lead wire group composed of lead wires (conducting wires) connected to the respective electrodes composing the first electrode group; and a second lead wire group composed of lead wires connected to the respective electrodes composing the second electrode group, wherein the first lead wire group and the second lead wire group extend through different lumina in the tube member, and voltages different from each other in polarity are applied between the first electrode group and the second electrode group, to perform defibrillation in a heart chamber (for example, Patent Literatures 1 to 4).

PRIOR ART DOCUMENTS

Patent Documents

Patent Document 1: JP-A-2017-153633
Patent Document 2: JP-A-2010-63708
Patent Document 3: JP-A-2014-97085
Patent Document 4: JP-A-2014-97084

SUMMARY OF INVENTION

Problems to be Solved by the Invention

In the catheters disclosed in Patent Literatures 1 to 4, a catheter inner cavity is of a multi-lumen structure, and conducting wires are disposed in different lumina by the polarity of voltage to be applied, whereby insulation property is ensured. However, since the catheters disclosed in Patent Literatures 1 to 4 have a multi-lumen structure, the space through which the conducting wires and the like pass is limited in the inner cavity of the tube member. Therefore, it is difficult to: increase the number of electrodes to be disposed on the catheter in order to enable intracardiac potentials to be measured at more positions with use of the one catheter; and reduce the diameter of the catheter in order to facilitate insertion of the catheter into a target site.

In addition, since the catheters disclosed in Patent Literatures 1 to 4 have a multi-lumen structure, the tube member becomes stiff, whereby problems arise in that: bending of a distal end portion of the catheter is difficult to finely control; and an electrode may be separated from the catheter when the catheter is bent.

These problems can be ameliorated by the following measure. Instead of disposing conducting wires in different lumina by polarity, conducting wires to be subjected to application of voltages different from each other in polarity are disposed in a same lumen, thereby obtaining a catheter having a configuration with a smaller number of lumina. However, by simply disposing the plurality of conducting wires in the same lumen, the insulation property between the conducting wires to be subjected to application of voltages different from each other in polarity may become insufficient.

The present invention has been made in view of the aforementioned circumstances, and an object of the present invention is to provide a catheter which has a plurality of electrodes to be subjected to application of voltages different from each other in polarity, and in which conducting wires connected to the electrodes are disposed in a same lumen but insulation property between the conducting wires is improved.

Solutions to the Problems

A catheter of the present invention that has solved the above problems comprising: an outer tube member having a lumen extending in a longitudinal direction; a handle provided on a proximal side of the outer tube member; a plurality of electrodes provided on the outer tube member; conducting wires connected to one or more of the electrodes and disposed in the lumen, the conducting wires each having a coating; and a wire having a distal end portion fixed to a distal end portion of the outer tube member, wherein a connection point between one of the electrodes and a conducting wire among the conducting wires and a connection point between another one of the electrodes and a conducting wire among the conducting wires are at different locations in a circumferential direction of the outer tube member, and the conducting wire connected to the one of the electrodes and the conducting wire connected to the another one of the electrodes are disposed in the same lumen of the outer tube member.

A method for manufacturing a catheter of the present invention that has solved the above problems comprising: an outer tube member having a lumen extending in a longitudinal direction, a handle provided on a proximal side of the outer tube member, a plurality of electrodes provided on a distal side of the outer tube member, conducting wires connected to one or more of the electrodes and disposed in the lumen and in the handle, the conducting wires each having a coating, an inner tube member disposed in the lumen, and a wire having a proximal end portion disposed in an inner cavity of the handle, and having a distal end portion fixed to a distal end portion of the outer tube member, a connection point between one of the electrodes and a conducting wire among the conducting wires and a connection point between another one of the electrodes and a conducting wire among the conducting wires being at different locations in a circumferential direction of the outer tube member, the conducting wire connected to the one of the electrodes and the conducting wire connected to the another one of the electrodes being disposed in the same lumen of the outer tube member, the manufacturing method comprising: a first step of disposing the conducting wires in the outer tube member; and a second step of disposing at least one of the inner tube member or the wire in the outer tube member, wherein the second step is performed after the first step.

Effects of the Invention

According to the present invention, in the catheter in which the plurality of conducting wires to be subjected to application of voltages different from each other in polarity are disposed in the same lumen, insulation property between the conducting wires can be improved.

BRIEF DESCRIPTION OF THE DRAWINGS

FIG. 1 is a plan view of a catheter according to an embodiment of the present invention.

FIG. 2 is a cross-sectional view of the catheter according to the embodiment of the present invention, along a longitudinal direction.

FIG. 3 is a III-III cross-sectional view of the catheter shown in FIG. 2.

FIG. 4 is a IV-IV cross-sectional view of the catheter shown in FIG. 2.

FIG. 5 is a V-V cross-sectional view of the catheter shown in FIG. 2.

MODE FOR CARRYING OUT THE INVENTION

Hereinafter, the present invention will be more specifically described based on the following embodiment. However, the present invention is not limited to the following embodiment and, as a matter of course, can also be carried out with appropriate modifications being made within the scope of the gist described above and below, and any of these modifications are included in the technical scope of the present invention. In any of the drawings, hatching, reference characters for members, or the like may be omitted for convenience. In this case, see the description and the other drawings. Since priority is given to facilitating the understanding of the characteristics of the present invention, the dimensions of various members in the drawings may be different from actual dimensions.

FIG. 1 is a plan view of a catheter according to an embodiment of the present invention. FIG. 2 is a cross-sectional view of the catheter according to the embodiment of the present invention, along a longitudinal direction. An entire configuration of the catheter according to the embodiment of the present invention will be described with reference to FIG. 1 and FIG. 2. A catheter 1 includes: an outer tube member 3 having a lumen 2 extending in the distal-proximal direction; a handle 4 provided on a proximal side of the outer tube member 3; a plurality of electrodes 5 provided on the outer tube member 3; conducting wires 6 connected to one or more of the electrodes 5 and disposed in the lumen 2, the conducting wires 6 each having a coating; and a wire 7 having a distal end portion fixed to a distal end portion of the outer tube member 3. A proximal end portion of the wire 7 is joined to the handle 4. The catheter 1 is caused to, for example, pass from a distal side thereof through the inside of a blood vessel of a patient to reach the heart so that the catheter 1 is used for a checkup or a therapy for arrhythmia, or defibrillation in the heart.

In the present invention, the proximal side refers to the hand side of a user in the extending direction of the outer tube member 3, and the distal side refers to the side opposite to the proximal side, that is, the treatment target side. The extending direction of the outer tube member 3 is referred to as an axial direction. A radial direction refers to the radial direction of the outer tube member 3, a radially inward direction refers to a direction toward the axial center side of the outer tube member 3, and a radially outward direction refers to a direction toward the side opposite to the radially inner side.

Regarding the catheter 1, the distal end of the catheter 1 can be bent or linearly extended by manipulating the handle 4. The distal end portion of the wire 7 is fixed to the distal end portion of the outer tube member 3, and thus, when the wire 7 is moved in the axial direction, the distal end portion of the outer tube member 3 fixed to the wire 7 moves in association with the movement of the wire 7 so that the distal side of the outer tube member 3 is bent to one side 3a.

FIG. 3 is a III-III cross-sectional view of the catheter shown in FIG. 2. FIG. 4 is a IV-IV cross-sectional view of the catheter shown in FIG. 2. As shown in FIG. 3 and FIG. 4, the electrodes 5 include at least a one-side electrode 5a and an other-side electrode 5b. In the catheter 1, a connection point 8a between the one-side electrode 5a and a conducting wire 6a and a connection point 8b between the other-side electrode 5b and a conducting wire 6b are at different locations in a circumferential direction of the outer tube member 3. Since the connection point 8a between the one-side electrode 5a and the conducting wire 6a and the connection point 8b between the other-side electrode 5b and the conducting wire 6b are thus located, a sufficient distance can be maintained between the conducting wire 6a and the conducting wire 6b so that a sufficient insulation property therebetween can be obtained, even though the conducting wire 6a connected to the one-side electrode 5a and the conducting wire 6b connected to the other-side electrode 5b to be subjected to application of a voltage different in polarity from a voltage for the one-side electrode 5a are disposed in the same lumen 2. Therefore, it becomes unnecessary to dispose the conducting wires in different lumina by polarity. Defibrillation can be performed by applying voltages different from each other in polarity to the one-side electrode 5a and the other-side electrode 5b.

FIG. 5 is a V-V cross-sectional view of the catheter shown in FIG. 2. As in the catheter shown in FIG. 3 and FIG. 4, the conducting wire 6a connected to the one-side electrode 5a and the conducting wire 6b connected to the other-side electrode 5b are disposed in the same lumen 2 of the outer tube member 3. Since the conducting wires 6a and 6b are disposed in the same lumen 2 of the outer tube member 3, a plurality of lumina 2 for disposing therein the conducting wires separately by polarity do not have to be provided, whereby an inner cavity of the outer tube member 3 can be widened. Accordingly, the number of conducting wires 6 that can be disposed in the catheter 1 can be increased, and thus the number of electrodes 5 of the catheter 1 can be increased more. In addition, since the number of lumina 2 in the catheter 1 can be reduced, the diameter of the catheter 1 can be further reduced, and the flexibility of the outer tube member 3 can be improved. If the number of lumina 2 is small, it becomes unnecessary to form partition walls for forming the lumina 2, and thus the flexibility of the outer tube member 3 can be improved. If the number of electrodes 5 of the catheter 1 is increased, the accuracies of a checkup and a therapy can be improved. In addition, if the diameter of the catheter 1 is reduced or the flexibility is improved, the movement of the distal end of the catheter 1 can be accurately controlled. In addition, if the outer tube member 3 becomes flexible, the electrodes 5 sink into the outer tube member 3, to become less likely to be separated therefrom. Accordingly, the electrodes 5 can be prevented from being separated at the time of bending.

The outer tube member 3 has a flexible tubular structure, and can be formed from, for example: a synthetic resin such as a polyolefin-based resin such as polyethylene or polypropylene, a polyamide-based resin such as nylon, a polyester-based resin such as PET, an aromatic polyether ketone-based resin such as PEEK, a polyether polyamide-based resin, a polyurethane-based resin, a polyimide-based resin, a fluorine-based resin such as PTFE, PFA, or ETFE, or a polyvinyl chloride-based resin; a metal such as stainless steel, carbon steel, or a nickel-titanium alloy; or the like. The outer tube member 3 may have a single-layer structure or a multi-layer structure. In a case where the outer tube member 3 has a multi-layer structure, the layers may be formed from the same material or different materials. For example, a structure in which a metal braid is used as an intermediate layer in a resin tube can be employed. The material of the outer tube member 3 is preferably a fluorine-based resin and more preferably PTFE. If the outer tube member 3 is thus formed, it is possible to obtain a catheter 1 of which insertion into a blood vessel is facilitated.

As the length in the axial direction of the outer tube member 3, a length that is appropriate for a therapy can be selected. For example, the length in the axial direction of the outer tube member 3 can be set to be not smaller than 500 mm and not larger than 1200 mm. The catheter 1 of the present invention allows the state of insulation between the conducting wires 6 to be maintained even if the length of the catheter 1 is increased.

The outer diameter of the outer tube member 3 is, for example, preferably not smaller than 0.6 mm, more preferably not smaller than 0.8 mm, and further preferably not smaller than 1.0 mm. If the lower limit value for the outer diameter of the outer tube member 3 is thus set, the outer tube member 3 comes to have an appropriate rigidity, and insertion of the catheter 1 into a blood vessel can be facilitated. In the case of a multi-lumen catheter, the outer diameter of the catheter is set to be about 2.0 mm in order to provide a plurality of lumina, whereby it is difficult reduce the outer diameter of the catheter. In contrast, the structure of the present invention makes it possible to provide a catheter having a smaller outer diameter. Meanwhile, the outer diameter of the outer tube member 3 is preferably not larger than 3.0 mm, more preferably not larger than 2.8 mm, and further preferably not larger than 2.5 mm. If the upper limit value for the outer diameter of the outer tube member 3 is thus set, the outer tube member 3 becomes less likely to come into contact with the inner wall of a blood vessel at the time of insertion of the catheter 1, whereby burden on the patient can be reduced.

In a case where the outer tube member 3 has a single lumen, the thickness of the outer tube member 3 is preferably not smaller than 50 μm, more preferably not smaller than 100 μm, and further preferably not smaller than 150 μm. If the lower limit value for the thickness of the outer tube member 3 is thus set, an appropriate rigidity is imparted to the outer tube member 3, and it is possible to obtain a catheter 1 of which insertion into a blood vessel is facilitated. Meanwhile, the thickness of the outer tube member 3 is preferably not larger than 350 μm, more preferably not larger than 250 μm, and further preferably not larger than 150 μm. If the upper limit value for the thickness of the outer tube member 3 is thus set, the lumen 2 of the outer tube member 3 can be widened.

The outer tube member 3 may employ a single-lumen structure having one lumen 2 therein or a multi-lumen structure having a plurality of lumina 2. Among the structures, the structure in which the number of lumina 2 of the outer tube member 3 is one is preferable. If the number of lumina 2 is one, no partition wall or the like is provided in the inner cavity of the outer tube member 3. Thus, the flexibility of the outer tube member 3 can be improved, whereby the bendability of the distal end portion of the catheter 1 becomes easy to control, and the electrodes 5 become less likely to be separated at the time of bending. In addition, the inner cavity of the outer tube member 3 can be widened, and thus it is possible to obtain a catheter having a plurality of electrodes and/or a catheter having a reduced diameter. In the lumen 2, for example, the conducting wires 6 connected to the electrodes 5, the wire 7, and the like are disposed.

The outer tube member 3 may have a distal tip 9 at the distal end thereof. The distal tip 9 is a lid-like member for closing an opening at the distal end of the outer tube member 3. If the outer tube member 3 has the distal tip 9, water in blood or the like is prevented, during use of the catheter 1, from entering the lumen 2 of the outer tube member 3 and coming into contact with the connection portions between the electrodes 5 and the conducting wires 6. Accordingly, it is possible to prevent: deterioration of insulation property between the plurality of conducting wires 6; and occurrence of a drift phenomenon in which the baseline potential in an electrocardiogram becomes unstable when an intracardiac potential is measured. In addition, the distal tip 9 serves as a guide for the distal end of the catheter 1, whereby insertion of the catheter 1 can be facilitated. Furthermore, the distal tip 9 can be used as a fixing portion for the wire 7. If a fixed end of the wire 7 is located at the distal tip 9 portion, the catheter 1 can be effectively bent by wire manipulation.

A material of the distal tip 9 is not particularly limited. For example, the aforementioned material of the outer tube member 3, a material of each electrode 5 described later, or the like can be used. If the distal tip 9 is formed from an electrically conductive material such as the material of the electrode 5 described later and the distal tip 9 is connected to any of the conducting wires 6, the distal tip 9 can serve also as an electrode 5.

The opening at the distal end of the outer tube member 3 may be closed by thermal fusion of the distal end portion of the outer tube member 3, or the like, without providing any distal tip 9 at the distal end of the outer tube member 3.

The handle 4 is provided on the proximal side of the outer tube member 3. In the handle 4, the wire 7 having the distal end portion fixed to the distal end portion of the outer tube member 3 and disposed in the inner cavity of the outer tube member 3 is fixed to the inner wall of the handle 4. Therefore, by manipulating the handle 4, the wire 7 is moved in the axial direction so that the outer tube member 3 can be bent, for example.

The electrodes 5 include at least the one-side electrode 5a and the other-side electrode 5b, and the one-side electrode 5a and the other-side electrode 5b are provided on the outer tube member 3 so as to be apart from each other on the distal side of the outer tube member 3. The catheter 1 has the plurality of electrodes apart from each other, i.e., the electrodes 5a and 5b, and thus, with the electrodes 5a and 5b being brought into contact with the inner wall of the heart of a patient, an intracardiac potential can be measured to identify an abnormal site of the heart that is the cause of arrhythmia, and defibrillation can be performed in a heart chamber. When defibrillation is performed, voltages different from each other in polarity may be applied to the electrodes 5a and 5b. For example, negative voltage may be applied to the one-side electrode 5a, and positive voltage may be applied to the other-side electrode 5b. The voltages to be applied to the one-side electrode 5a and the other-side electrode 5b can be switched in polarity. Specifically, after negative voltage is applied to the one-side electrode 5a, positive voltage may be applied thereto.

Although the type of each of the plurality of electrodes 5 including the one-side electrode 5a and the other-side electrode 5b is not particularly limited, both an electrode for performing defibrillation and an electrode for measuring an intracardiac potential are preferably provided. For example, the one-side electrode 5a and the other-side electrode 5b may be used as electrodes for performing defibrillation by being respectively subjected to application of voltages different from each other in polarity, and a separate electrode different from the one-side electrode 5a and the other-side electrode 5b may be used as an electrode for measuring an intracardiac potential. In addition, the electrodes for performing defibrillation can serve also as electrodes for measuring a potential. If the plurality of electrodes 5 are thus configured, it is possible to, with the one catheter, perform: defibrillation when arrhythmia such as atrial fibrillation occurs; and measurement of an intracardiac potential to identify an abnormal site that is the cause of arrhythmia. The number of one-side electrodes 5a, the number of other-side electrodes 5b, and the number of separate electrodes may be one or more. The number of one-side electrodes 5a, the number of other-side electrodes 5b, and the number of separate electrodes may be the same as or different from one another.

The arrangement of the plurality of electrodes 5 including the one-side electrode 5a and the other-side electrode 5b is not particularly limited, and, for example, electrodes for performing defibrillation and electrodes for measuring an intracardiac potential are preferably arranged alternately. A specific example of the arrangement is as follows. With the one-side electrode 5a being a negative electrode for performing defibrillation, the other-side electrode 5b being a positive electrode for performing defibrillation, and the separate electrode different from the one-side electrode 5a and the other-side electrode 5b being an electrode for measuring an intracardiac potential, the electrode for measuring an intracardiac potential is preferably disposed between the negative electrode and the positive electrode for performing defibrillation such that the one-side electrode 5a which is the negative electrode for performing defibrillation, the separate electrode which is different from the one-side electrode 5a and the other-side electrode 5b and which is the electrode for measuring an intracardiac potential, and the other-side electrode 5b which is the positive electrode for performing defibrillation, are arranged in this order from the distal side to the proximal side of the outer tube member 3. If the plurality of electrodes 5 are thus arranged, the electrode for measuring an intracardiac potential is located at the inner wall of the heart when the electrodes for performing defibrillation are disposed so as to hold the heart therebetween, with the negative electrode for performing defibrillation being disposed at the coronary sinus and the positive electrode for performing defibrillation being disposed at the right atrium. Therefore, when electrical stimulation is applied between the positive electrode and the negative electrode for performing defibrillation, it is possible to quickly check whether or not defibrillation has been successfully performed.

The electrodes 5 may be ring-shaped electrodes or may be plate electrodes that each have a rectangular shape, a square shape, or the like and that are independently formed into the shapes of islands on the outer tube member 3. At least one of the back surface (inner surface) or the front surface (outer surface) of each plate electrode may be a curved surface so as to be easily fitted along the curve of the surface of the outer tube member 3. In particular, the electrodes 5 are preferably ring-shaped. If the electrodes 5 are ring-shaped, the area of the electrodes 5 on the circumference of the outer tube member 3 can be made large, whereby it becomes easy to bring the electrodes 5 into contact with the inner wall of the heart, and the like.

Examples of a material of each electrode 5 include metal materials such as copper, gold, platinum, aluminum, iron, and an alloy thereof. In order to obtain a favorable contrasting property with respect to X-rays during use of the catheter 1, the electrode 5 is preferably formed from platinum or an alloy thereof.

The conducting wires 6 electrically connect the electrodes 5 and an external device (not shown) for the catheter 1 to each other, and are disposed in the lumen 2 of the outer tube member 3. As shown in FIG. 2 to FIG. 5, the conducting wires 6 are connected to the electrodes 5 and pass in the lumen 2 of the outer tube member 3.

A material for a core of each conducting wire 6 is not particularly limited as long as the material is an electrically conductive material. For example, an iron wire, a copper wire, a silver wire, a stainless steel wire, a tungsten wire, a nickel-titanium wire, or the like can be used. Among the wires, a stainless steel wire is particularly preferable in that the stainless steel wire has straightness and rigidity, and thus the stainless steel wire allows the conducting wire 6 to easily pass in the outer tube member 3 and is less likely to be broken at the connection portion between the conducting wire 6 and the corresponding electrode 5.

The conducting wire 6 has a coating at a portion thereof other than both end portions connected to other objects such as the electrode 5. Specifically, for example, it is preferable that: the coating at one end of the conducting wire 6 is partially removed; and the portion is connected to the electrode 5 by welding or the like.

The coating of the conducting wire 6 only has to be formed from an insulating material, and examples of the insulating material include synthetic resins such as polyolefin-based resins such as polyethylene and polypropylene, polyamide-based resins such as nylon, polyester-based resins such as PET, aromatic polyether ketone-based resins such as PEEK, polyether polyamide-based resins, polyurethane-based resins, polyimide-based resins, fluorine-based resins such as PTFE, PFA, and ETFE, and polyvinyl chloride-based resins. Among the insulating materials, the coating of the conducting wire 6 is preferably formed from a fluorine-based resin and more preferably formed from PFA. If the coating of the conducting wire 6 is thus formed, the insulation property of the conducting wire 6 can be ensured. Furthermore, in the lumen 2 of the outer tube member 3, the slidability of the conducting wire 6 relative to other objects such as another conducting wire 6 and the wire 7 is improved, whereby the coating of the conducting wire 6 can be prevented from being damaged.

The thickness of the coating of the conducting wire 6 is preferably not smaller than 20 µm, more preferably not smaller than 25 µm, and further preferably not smaller than 30 µm. If the lower limit value for the thickness of the coating of the conducting wire 6 is thus set, a sufficient insulation property can be imparted to the conducting wire 6. Meanwhile, the thickness of the coating of the conducting wire 6 is preferably not larger than 50 µm, more preferably not larger than 40 µm, and further preferably not larger than 35 µm. If the upper limit value for the thickness of the coating of the conducting wire 6 is thus set, it is possible to make the diameter of the conducting wire 6 small while ensuring a sufficient insulation property of the conducting wire 6. Therefore, the conducting wire 6 can be caused to easily pass in the lumen 2 of the outer tube member 3 during manufacturing of the catheter 1.

As a method for connecting the conducting wire 6 to the electrode 5, for example, welding, brazing such as soldering, connection by crimping or the like, or the like can be performed. Among the methods, welding is preferable. If the conducting wire 6 is connected to the electrode 5 by welding, the connection between the conducting wire 6 and the electrode 5 can be easily made firm. In addition, the space on the inner side of the electrode 5 can be ensured to be widest, and the electrode 5 is easily attached to the outer tube member 3. As a result, workability for manufacturing can be improved. The conducting wire 6 and the electrode 5 may be connected to each other with an electrically conductive member interposed therebetween.

The connection portion between the conducting wire 6 and the electrode 5 is preferably coated with a resin or the like such that oxidation degradation does not occur owing to water or the like contained in the atmosphere or the like. Examples of the resin to be used for coating of the connection portion between the conducting wire 6 and the electrode 5 include polyurethane resins, epoxy resins, and the like.

The conducting wires 6 include at least the conducting wire 6a connected to the one-side electrode 5a and the conducting wire 6b connected to the other-side electrode 5b, and the connection point 8a between the one-side electrode 5a and the conducting wire 6a and the connection point 8b between the other-side electrode 5b and the conducting wire 6b may be at different locations in the circumferential direction of the outer tube member 3. Specifically, in a cross section perpendicular to the axial direction of the outer tube member 3, the distance between the connection point 8a between the one-side electrode 5a and the conducting wire 6a and the connection point 8b between the conducting wire 6b and the other-side electrode 5b adjacent to the one-side electrode 5a is preferably not shorter than L/15, more preferably not shorter than L/10, and further preferably not shorter than L/8, where L represents the length of the outer circumference of the outer tube member 3. If the lower limit value for the distance between the connection point 8a between the one-side electrode 5a and the conducting wire 6a and the connection point 8b between the other-side electrode 5b and the conducting wire 6b is thus set, the conducting wire 6a connected to the one-side electrode 5a and the conducting wire 6b connected to the other-side electrode 5b become less likely to come into contact with each other, whereby insulation property therebetween can be more improved. Although the upper limit value for the distance between the connection point 8a between the one-side electrode 5a and the conducting wire 6a and the connection point 8b between the conducting wire 6b and the other-side electrode 5b adjacent to the one-side electrode 5a is not particularly limited, the distance can be set to be, for example, not longer than L/2. In a case where the number of one-side electrodes 5a is two or more and the number of other-side electrode 5b is also two or more, all connection points may be at different locations in the circumferential direction, or connection points for electrodes to be subjected to application of voltage of the same polarity may be at the same location in the circumferential direction. The electrodes to be subjected to application of voltage of the same polarity refer to all of the one-side electrodes 5a or all of the other-side electrodes 5b.

In the cross section perpendicular to the axial direction of the outer tube member 3, the angle θ1 between a straight line S1 passing, as shown in FIG. 3, the center point of the smallest circle circumscribing the outer tube member 3 and the connection point 8a between the one-side electrode 5a and the conducting wire 6a, and a straight line S2 passing, as shown in FIG. 4, the center point of the smallest circle circumscribing the outer tube member 3 and the connection point 8b between the other-side electrode 5b and the conducting wire 6b, is preferably not smaller than 30 degrees, more preferably not smaller than 45 degrees, and further preferably not smaller than 60 degrees. If the lower limit value for the angle θ1 is thus set, the conducting wire 6a connected to the one-side electrode 5a and the conducting wire 6b connected to the other-side electrode 5b become less likely to come into contact with each other, whereby insulation property between the conducting wire 6a and the conducting wire 6b can be maintained. Although the upper limit value for the angle θ1 between the straight line S1 and the straight line S2 is not particularly limited, the angle θ1 can be set to be, for example, not larger than 180 degrees.

It is preferable that, as shown in FIG. 3 and FIG. 4: the outer tube member 3 has holes 10 penetrating therethrough in the radial direction; and each conducting wire 6 connected to the corresponding electrode 5 is inserted in the corresponding hole 10 and located in the lumen 2 of the outer tube member 3. If the catheter 1 is thus configured, a step of disposing the conducting wire 6 connected to the electrode 5 in the lumen 2 of the outer tube member 3 can be easily performed during manufacturing of the catheter 1.

The conducting wires 6 are connected to the one or more of the electrodes 5 and disposed in the lumen 2. Each one of the conducting wires 6 is preferably connected to the corresponding electrode 5. Accordingly, the electrodes 5 can be individually controlled. For example, the one-side electrode 5a can be used for measuring an intracardiac potential or used for performing defibrillation by being subjected to application of voltage. Alternatively, the conducting wires 6 may be connected to a plurality of the electrodes 5, and, for example, the electrodes 5 can be connected in series. The electrodes 5 connected in series can be suitably used for defibrillation. In this case, some of the plurality of the electrodes 5 may be connected in series to one of the conducting wires 6, other electrodes among the plurality of the electrodes 5 may be connected in series to another conducting wire 6, and each one of conducting wires 6 may be connected to the corresponding electrode 5 among the remaining ones of the plurality of the electrodes 5. Accordingly, electrodes 5 for use in measurement of a heart potential and electrodes 5 for use in defibrillation can be used as dedicated electrodes. Also in a case where each one of the conducting wires 6 is connected to all the electrodes 5, each electrode 5 may be used as a dedicated electrode for measuring an intracardiac potential or for defibrillation.

As shown in FIG. 2, the wire 7 has the distal end portion fixed to the distal end portion of the outer tube member 3. Although the wire 7 only has to be such that the distal end portion of the wire 7 is fixed to the distal end portion of the outer tube member 3, the distal end of the wire 7 is preferably fixed to the distal end of the inner cavity of the outer tube member 3. If the wire 7 is thus fixed to the outer tube member 3, the distal side of the outer tube member 3 can be greatly bent. In the present description, the phrase "the distal end portion of the wire 7 is fixed to the distal end portion of the outer tube member 3" encompasses: a state where the distal end portion of the wire 7 is directly fixed to the distal end portion of the outer tube member 3; and an indirectly fixed state such as a state where the distal end portion of the wire 7 is fixed to the distal end portion of the outer tube member 3 with another object such as the distal tip 9 therebetween.

Examples of a usable material of the wire 7 include: metal wire materials formed from stainless steel, carbon steel, a nickel-titanium alloy, or the like; and yarns formed from synthetic resins such as a polyolefin-based resin such as polyethylene or polypropylene, a polyamide-based resin such as nylon, a polyester-based resin such as PET, an aromatic polyether ketone-based resin such as PEEK, a polyether polyamide-based resin, a polyurethane-based resin, a polyimide-based resin, a fluorine-based resin such as PTFE, PFA, or ETFE, or a polyvinyl chloride-based resin. The wire 7 may have a structure in which a metal material and a synthetic resin material are combined with each other. For example, a wire 7 obtained by knitting a wire material formed from a metal and a wire material formed from a synthetic resin, or a wire 7 obtained by coating a metal wire material with a resin, can be used. Among the materials of the wire 7, metal wire materials are preferable, and stainless steel is further preferable. If the wire 7 is thus formed, the wire 7 can be made less likely to be damaged or deformed even if the wire 7 is repetitively bent for bending the outer tube member 3.

The method for fixing the distal end portion of the wire 7 and the distal end portion of the outer tube member 3 to each other is not particularly limited, and examples of the method include brazing such as soldering, welding, adhesion using an adhesive, connection by crimping or the like, and the like. The fixation between the distal end portion of the wire 7 and the distal end portion of the outer tube member 3 is preferably as follows. With the outer tube member 3 having the distal tip 9 formed from metal at the distal end thereof and the wire 7 being formed from a metal wire material, the wire 7 and the distal tip 9 are fixed to each other by soldering. If the distal end portion of the wire 7 and the distal end portion of the outer tube member 3 are thus fixed to each other, the fixation between the wire 7 and the outer tube member 3 becomes firm. Accordingly, the wire 7 becomes less likely to be detached from the outer tube member 3 even when the wire 7 is moved in the axial direction in order to bend the distal side of the outer tube member 3.

Although the diameter of the wire 7 is not particularly limited, the diameter is preferably not smaller than 100 µm, more preferably not smaller than 150 µm, and further preferably not smaller than 200 µm. If the lower limit value for the diameter of the wire 7 is thus set, the strength of the wire 7 can be made sufficient. Meanwhile, the diameter of the wire 7 is preferably not larger than 500 µm, more preferably not larger than 450 µm, and further preferably not larger than 400 µm. If the upper limit value for the diameter of the wire 7 is thus set, the lumen 2 of the outer tube member 3 can be ensured to be sufficiently wide.

As shown in FIG. 2, when the wire 7 is moved in the axial direction, the distal side of the outer tube member 3 is bent to the one side 3a. For moving the wire 7 in the axial direction, a manipulation such as pulling of the wire 7 to the proximal side may be performed by, for example, winding back the wire 7 through manipulation of the handle 4.

Alternatively, the distal side of the outer tube member 3 can be bent also by pushing the wire 7 to the distal side. By bending the distal side of the outer tube member 3 to the one side 3a, in the heart, the electrode 5 that is disposed on the distal side of the outer tube member 3 can be caused to approach the inner wall of the heart, whereby it becomes easy to bring the electrode 5 into contact with a target site in the heart.

The number of wires 7 may be one or more. In a case where the number of wires 7 is one, the volume of the wire 7 in the inner cavity of the outer tube member 3 can be made small, whereby the lumen 2 of the outer tube member 3 can be widened. In a case where the number of wires 7 is two or more, if, for example, a distal end portion of one of the wires is fixed to one side of the distal end portion of the outer tube member 3 in a cross section perpendicular to the axial direction of the outer tube member 3 and a distal end portion of another wire is fixed to another side of the distal end portion of the outer tube member 3 in the cross section perpendicular to the axial direction of the outer tube member 3, the distal side of the outer tube member 3 can be bent in a plurality of directions toward the one side and the other side, whereby it becomes easy to bring the electrode 5 into contact with various sites in the heart.

It is preferable that, as shown in FIG. 2 to FIG. 4, at least one of the conducting wires 6 is, in a cross section perpendicular to the axial direction of the outer tube member 3 at a bending portion 11 of the outer tube member 3, present on at least one position on the one side 3a among the one side 3a of the outer tube member 3 and another side 3b opposite to the one side 3a. The bending portion 11 refers to a portion that extends to the distal end of the outer tube member 3 from a portion that serves as an origin of bending when the outer tube member 3 is bent by moving the wire 7 in the axial direction. In the example shown in FIG. 3, the conducting wire 6a connected to the one-side electrode 5a is present on the one side 3a of the outer tube member 3. If the conducting wires 6 are thus disposed, a load is less likely to be applied to each conducting wire 6 when the outer tube member 3 is bent, whereby damage to the coating of the conducting wire 6 and wire breakage can be prevented. Therefore, the insulation property of the conducting wire 6 can be maintained.

It is preferable that, as shown in FIG. 5, the conducting wire 6a connected to the one-side electrode 5a and the conducting wire 6b connected to the other-side electrode 5b are at different locations in the circumferential direction of the outer tube member 3. Specifically, the connection point 8a between the one-side electrode 5a and the conducting wire 6a and the connection point 8b between the other-side electrode 5b and the conducting wire 6b are at different locations in the circumferential direction of the outer tube member 3, and the conducting wire 6a connected to the one-side electrode 5a and the conducting wire 6b connected to the other-side electrode 5b are at different locations in the circumferential direction of the outer tube member 3. Accordingly, the conducting wire 6a and the conducting wire 6b become further less likely to come into contact with each other in the lumen 2. Therefore, insulation property therebetween can be further improved.

The catheter 1 preferably includes an inner tube member 12 disposed in the lumen 2. If the inner tube member 12 is disposed in the lumen 2, the rigidity of the outer tube member 3 can be improved, and insertion of the catheter 1 into a blood vessel can be facilitated.

The type of the inner tube member 12 is not particularly limited, and examples thereof include: cylindrical tubes and pipes; coils obtained by spirally winding a wire material; and the like. Among the types, the inner tube member 12 is preferably a coil or a pipe, and is more preferably formed by combination thereof. If the inner tube member 12 is thus formed, it is possible to impart an appropriate flexibility while improving the rigidity of the outer tube member 3. Therefore, it is possible to obtain a catheter 1 of which insertion into a blood vessel is facilitated and which is easily inserted even into a curvy blood vessel.

As a material of the inner tube member 12, the same synthetic resin or metal as that for the outer tube member 3, or the like can be used. The inner tube member 12 may have a layered structure. The material of the inner tube member 12 and the material of the outer tube member 3 may be the same as or different from each other. The inner tube member 12 is preferably formed from a metal. Specifically, the inner tube member 12 is more preferably a coil that is obtained by spirally winding a wire material formed from stainless steel. If the inner tube member 12 is thus formed, a catheter 1 is obtained in which bending of the outer tube member 3 is easily adjusted while a sufficient rigidity is imparted to the outer tube member 3.

In a case where the inner tube member 12 is a pipe, the outer diameter of the distal end of the inner tube member 12 is preferably smaller than the outer diameter of the proximal end thereof. If the inner tube member 12 is thus formed, the pushability of the catheter 1 can be improved. Examples of a method for forming the inner tube member 12 having a smaller outer diameter at the distal end than at the proximal end thereof include methods that involve: joining of a tube having a larger outer diameter and a tube having a smaller outer diameter; swaging of a metal tube; heating of a part of a tube formed from a heat-shrinkable resin, to reduce the diameter of the part; or the like.

The inner tube member 12 is preferably provided with: a metal tube having a smaller outer diameter at the distal end than at the proximal end thereof, and a metal coil disposed at the distal side of the metal tube. If the inner tube member 12 is thus formed, the inner tube member has a higher stiffness at the proximal side thereof and has a lower stiffness at the distal side thereof, whereby force exerted from the hand side of the catheter 1 can be efficiently transmitted to the distal side. As a result, loss in torque transmission can be reduced.

The wire 7 is preferably disposed inside the inner tube member 12. If the wire 7 is thus disposed, the wire 7 becomes less likely to come into contact with the conducting wire 6, whereby the coating of the conducting wire 6 can be prevented from being damaged.

The inner tube member 12 and the wire 7 are preferably disposed in the lumen 2 in which the conducting wires 6 are disposed. That is, the conducting wires 6, the wire 7, and the inner tube member 12 are preferably disposed in the same lumen 2 of the outer tube member 3. Further, the wire 7 is preferably disposed in the inner cavity of the inner tube member 12. If the catheter 1 is thus configured, it is possible to: reduce the number of lumina 2 of the outer tube member 3, thereby reducing the diameter of the catheter 1; and widen the inner cavity of the outer tube member 3 and increase the number of electrodes 5, thereby multi-polarizing the catheter 1. In addition, the flexibility of the outer tube member 3 can be improved.

It is preferable that, as shown in FIG. 2 and FIG. 5, the inner tube member 12 has a protective member 13 disposed radially outward of the inner tube member 12. If the inner tube member 12 has the protective member 13, the coatings of the conducting wires 6 can be prevented from being damaged by the inner tube member 12 coming into contact with the conducting wires 6.

A material of the protective member 13 of the inner tube member 12 is preferably an insulating material. Regarding specific examples of the material of the protective member 13 of the inner tube member 12, the materials included in the examples of the material of the coating of each of the conducting wire 6 can be used. Among the materials, the protective member 13 is preferably formed from a polyolefin-based resin such as polyethylene. If the protective member 13 is formed from the material, insulation property between the conducting wire 6 and the inner tube member 12 can be maintained and safety can be improved, even if the coating of the conducting wire 6 is damaged in a case where the inner tube member 12 is formed from a metal.

In addition, the protective member 13 of the inner tube member 12 is preferably formed from an insulating material that is different from the material of the coating of the conducting wire 6. Specifically, it is more preferable that: the protective member 13 of the inner tube member 12 is formed from a polyolefin-based resin; and the coating of the conducting wire 6 is formed from a fluorine-based resin. If the protective member 13 is thus formed, the slidability between the protective member 13 and the conducting wire 6 is improved. Accordingly, the coating of the conducting wire 6 can be prevented from being damaged owing to contact between the conducting wire 6 and the protective member 13 during manufacturing or usage of the catheter 1.

The thickness of the protective member 13 of the inner tube member 12 is preferably smaller than the thickness of the outer tube member 3 and larger than the thickness of the coating of the conducting wire 6. If the protective member 13 is thus formed, the coating of the conducting wire 6 becomes less likely to be damaged when the protective member 13 and the conducting wire 6 come into contact with each other. In addition, the distance between the protective member 13 and the inner surface of the outer tube member 3 can be elongated, whereby the conducting wire 6 and the protective member 13 become less likely to come into contact with each other.

It is preferable that, as shown in FIG. 2, the catheter 1 includes an elastic member 14 having a distal end portion fixed to the distal end portion of the outer tube member 3 and having a proximal end portion fixed to the inner tube member 12. The elastic member 14 extends along the distal-proximal direction. If the catheter 1 includes the elastic member 14, it is possible to finely adjust the extent to which the distal side of the outer tube member 3 is to be bent by moving the wire 7 in the axial direction.

The type of the elastic member 14 is not particularly limited, and examples thereof include flat springs, coil springs, and the like. Among the types, the elastic member 14 is preferably a flat spring. The flat spring is a spring made using a sheet material, and a cross-sectional shape, of the flat spring, that is taken in the axial direction is rectangular. The flat spring is bent at a long-side portion thereof in the cross-sectional shape. Thus, when the wire 7 is moved in the axial direction, the long-side portion of the flat spring is bent to the wire 7 side. Therefore, if the elastic member 14 is the flat spring, the bending direction of the distal side of the outer tube member 3 can be fixed.

Examples of a material of the elastic member 14 include stainless steel, carbon steel, copper alloys, titanium alloys, and the like. Among the materials, the material of the elastic member 14 is preferably stainless steel. If the elastic member 14 is thus formed, the extent of the bending of the distal side of the outer tube member 3 becomes easier to adjust.

Although the distal end portion of the elastic member 14 only has to be fixed to the distal end portion of the outer tube member 3, it is preferable that the distal end of the elastic member 14 is fixed to the distal end of the inner wall of the outer tube member 3. If the distal end of the elastic member 14 is thus fixed to the outer tube member 3, bending of the distal side of the outer tube member 3 becomes easy to control.

A method for fixing the distal end portion of the elastic member 14 and the distal end portion of the outer tube member 3 to each other is not particularly limited, and examples of the method include brazing such as soldering, welding, adhesion using an adhesive, connection by crimping or the like, and the like. The fixation between the distal end portion of the elastic member 14 and the distal end portion of the outer tube member 3 is preferably as follows. With the outer tube member 3 having the distal tip 9 formed from metal at the distal end thereof and the elastic member 14 being formed from metal, the elastic member 14 and the distal tip 9 are fixed to each other by soldering. If the distal end portion of the elastic member 14 and the distal end portion of the outer tube member 3 are thus fixed to each other, the elastic member 14 can be firmly fixed to the outer tube member 3. Accordingly, the elastic member 14 can be made less likely to be detached from the outer tube member 3 even when the distal side of the outer tube member 3 is bent. A step of fixing the elastic member 14 and the outer tube member 3 to each other may be performed simultaneously with a step of fixing the wire 7 and the outer tube member 3 to each other.

It is preferable that, as shown in FIG. 2, the catheter 1 includes a tubular member 15 disposed on the proximal side relative to the distal end portion of the wire 7. The tubular member 15 is preferably disposed in the lumen 2 of the outer tube member 3. If the catheter 1 includes the tubular member 15, the coating of the conducting wire 6 can be prevented from being damaged by the conducting wire 6 coming into contact with another object such as the wire 7 disposed in the lumen 2 of the outer tube member 3.

At least one of the wire 7 or the elastic member 14 is preferably disposed in an inner cavity of the tubular member 15. If the wire 7 is disposed in the inner cavity of the tubular member 15, the coating of the conducting wire 6 can be prevented from being damaged owing to contact between the wire 7 and the conducting wire 6. In addition, the location of the wire 7 in the lumen 2 of the outer tube member 3 is fixed, whereby it is possible to reduce the distance for the wire 7 to be moved in the axial direction in order to bend the distal side of the outer tube member 3. As a result, the outer tube member 3 can be finely adjusted in terms of the manner of the bending thereof and can be promptly bent. If the elastic member 14 is disposed in the inner cavity of the tubular member 15, the elastic member 14 and the conducting wire 6 are prevented from coming into contact with each other, whereby the coating of the conducting wire 6 becomes less likely to be damaged. In particular, it is more preferable that the wire 7 and the elastic member 14 are disposed in the inner cavity of the tubular member 15.

Although a material of the tubular member 15 is not particularly limited, the material is preferably an insulating material. For example, the insulating materials included in the examples of the material of the coating of the conducting wire 6 can be used. Among the materials, the material of the tubular member 15 is preferably a different type of material from the material of the coating of the conducting wire 6. For example, in a case where the material of the coating of the conducting wire 6 is PTFE, the material of the tubular member 15 is preferably different from PTFE. If the tubular member 15 is thus formed, the slipperiness between the conducting wire 6 and the tubular member 15 can be improved. Accordingly, the coating of the conducting wire 6 can be prevented from being damaged owing to contact between the conducting wire 6 and the tubular member 15 during manufacturing or usage of the catheter 1.

The thickness of the tubular member 15 is preferably smaller than the thickness of the outer tube member 3 and larger than the thickness of the coating of the conducting wire 6. If the tubular member 15 is thus formed, the distance between the tubular member 15 and the inner surface of the outer tube member 3 can be elongated, whereby the conducting wire 6 and the tubular member 15 become less likely to come into contact with each other. In addition, the coating of the conducting wire 6 can be made less likely to be damaged even if the tubular member 15 and the conducting wire 6 come into contact with each other.

It is preferable that, as shown in FIG. 2: a proximal end portion of the tubular member 15 is located on the distal side relative to a distal end portion of the protective member 13 of the inner tube member 12; and the distal end of the protective member 13 of the inner tube member 12 and the proximal end of the tubular member 15 are apart from each other. That is, it is preferable that: a space is present between the distal end of the protective member 13 of the inner tube member 12 and the proximal end of the tubular member 15; and the inner tube member 12 is exposed from the protective member 13 in the lumen 2 of the outer tube member 3. A distal end portion of the inner tube member 12 is preferably fixed to the inner wall of the outer tube member 3. If the inner tube member 12 is exposed from the protective member 13 and the inner tube member 12 is fixed to the inner wall of the outer tube member 3, the stiffness of a portion, of the outer tube member 3, to which the distal end portion of the inner tube member 12 is fixed is increased, and the portion having an increased stiffness can be set as an origin from which the outer tube member 3 is to be bent. In addition, on the distal side of the outer tube member 3, the location of the inner tube member 12 in the lumen 2 of the outer tube member 3 is fixed, and variation in the manner of bending, of the outer tube member 3, that is caused by movement in the axial direction of the wire 7 disposed in the inner cavity of the inner tube member 12 is reduced, whereby the manner of the bending of the outer tube member 3 can be controlled to be uniform. In addition, if the inner tube member 12 is fixed to the inner wall of the outer tube member 3, axial rotation (torque) of the catheter 1 applied on the hand side by an operator is easily transmitted to the outer tube member 3 through the inner tube member 12, whereby the axial rotation of the distal end portion of the outer tube member 3 becomes easy to control.

Examples of a method for fixing the distal end portion of the inner tube member 12 to the inside of the lumen 2 of the outer tube member 3 include: a method in which an adhesive is caused to flow into the outer tube member 3 so as to fix the inner surface of the outer tube member 3 and the distal end portion of the inner tube member 12 to each other; a method in which a ring-shaped component or the like is attached on the outer tube member 3 at a location, at which the distal end portion of the inner tube member 12 is present in the inner cavity, and is crimped so that the outer tube member 3 and the distal end portion of the inner tube member 12 are fixed from the radially outward of the outer tube member 3; and the like. Among the methods, the method in which an adhesive is caused to flow into the outer tube member 3 so as to fix the outer tube member 3 and the distal end portion of the inner tube member 12 to each other, is preferable. If the outer tube member 3 and the distal end portion of the inner tube member 12 are thus fixed to each other, the distal end portion of the inner tube member 12 can be easily and firmly fixed to the outer tube member 3.

Examples of the adhesive used for fixing the distal end portion of the inner tube member 12 to the inside of the lumen 2 of the outer tube member 3 include epoxy resin-based adhesives, acrylic resin-based adhesives, urethane resin-based adhesives, and the like. Among the adhesives, an epoxy resin-based adhesive is preferably used. If such an adhesive is used, the adhesive is easily handled, and the distal end portion of the inner tube member 12 can be sufficiently fixed to the inside of the lumen 2 of the outer tube member 3.

The inner tube member 12 is preferably fixed to the inside of the handle 4. Specifically, the proximal end portion of the inner tube member 12 is preferably fixed to the inside of the handle 4. If the inner tube member 12 is thus fixed, when a load such as a twist is applied to the outer tube member 3, the load is less likely to be applied to the conducting wires 6 in the lumen 2 of the outer tube member 3, whereby insulation property can be prevented from deteriorating owing to damage to the coatings of the conducting wires 6, or the like.

Examples of a method for fixing the inner tube member 12 to the inside of the handle 4 include: methods that involve adhesion using an adhesive, welding in which a synthetic resin is melted and fixed, fixation using a separate member such as a screw, fitting of a recess and a projection, or the like; combinations of these methods; and the like. Among the methods, the fixation of the inner tube member 12 to the inside of the handle 4 is preferably performed by fitting the inner tube member 12 to the handle 4. If the inner tube member 12 is thus fixed to the inside of the handle 4, the inner tube member 12 can be easily and firmly fixed to the inside of the handle 4.

A manufacturing method for the catheter 1 according to the present invention is a manufacturing method for the catheter 1 including: an outer tube member 3 having a lumen 2 extending in a longitudinal direction; a handle 4 provided on a proximal side of the outer tube member 3; a plurality of electrodes 5 provided on a distal side of the outer tube member 3; conducting wires 6 connected to one or more of the electrodes 5 and disposed in the lumen 2 and in the handle 4, the conducting wires 6 each having a coating; an inner tube member 12 disposed in the lumen 2; and a wire 7 having a proximal end portion disposed in an inner cavity of the handle 4, and having a distal end portion fixed to a distal end portion of the outer tube member 3. A connection point 8a between a one-side electrode 5a and a conducting wire 6a and a connection point 8b between an other-side electrode 5b and a conducting wire 6b are at different locations in a circumferential direction of the outer tube member 3. The conducting wire 6a connected to the one-side electrode 5a and the conducting wire 6b connected to the other-side electrode 5b are disposed in the same lumen 2 of the outer tube member 3. The manufacturing method includes: a first step of disposing the conducting wires 6 in the outer tube member 3; and a second step of disposing at least one of the inner tube member 12 or the wire 7 in the outer tube member 3. The second step is performed after the first step.

In the first step, the conducting wires 6 are disposed in the lumen 2 of the outer tube member 3. The conducting wires 6 may be connected to the electrodes 5 and inserted into the holes 10 from a radially outward of the outer tube member 3, to be disposed in the outer tube member 3. Alternatively, the conducting wires 6 may be disposed in the outer tube member 3 and inserted into the holes 10 from a radially inner side of the outer tube member 3, to be connected to the electrodes 5. In particular, it is preferable that the conducting wires 6 are connected to the electrodes, and then the conducting wires 6 are inserted into the holes 10 of the outer tube member 3, and the conducting wires 6 are disposed in the outer tube member 3. If the first step is thus performed, connection between the conducting wires 6 and the electrodes 5 is easily performed, and workability can be improved.

In the second step, at least one of the inner tube member 12 or the wire 7 is disposed in the lumen 2 of the outer tube member 3. Specific examples of the disposition include: a disposition in which an opening that allows communication with the lumen 2 is provided on the distal side or the proximal side of the outer tube member 3, and at least one of the inner tube member 12 or the wire 7 is inserted through the opening; and the like. In particular, it is preferable that the inner tube member 12 and the wire 7 are disposed in the outer tube member 3. In the case where both the inner tube member 12 and the wire 7 are disposed in the outer tube member 3, the inner tube member 12 may be disposed in the outer tube member 3, and then the wire 7 may be disposed in the inner tube member 12. Alternatively, the wire 7 may be disposed in the inner tube member 12, and then the inner tube member 12, in the inner cavity of which the wire 7 has been disposed, may be disposed in the outer tube member 3. In particular, it is preferable that the inner tube member 12 is disposed in the outer tube member 3, and then the wire 7 is disposed in the inner tube member 12. If the second step is thus performed, the inner tube member 12 and the wire 7 are easily disposed in the outer tube member 3. Furthermore, damage to the coatings of the conducting wires 6 and a crack on the inner tube member 12 or the inner surface of the outer tube member 3 can be prevented from occurring by the inner tube member 12 and the wire 7 rubbing against the inner surface of the outer tube member 3 or the conducting wires 6.

The second step is performed after the first step. If the conducting wires 6 having lower rigidities than the inner tube member 12 and the wire 7 and more likely to be damaged than the inner tube member 12 and the wire 7 are disposed in a state where the inner cavity of the outer tube member 3 is widest, the coatings of the conducting wires 6 can be prevented from being damaged. A separate step of, for example, providing the handle 4 on the proximal side of the outer tube member 3 may be performed between the first step and the second step.

A catheter according to the embodiment of the present invention includes: an outer tube member having a lumen extending in a longitudinal direction; a handle provided on a proximal side of the outer tube member; a plurality of electrodes provided on the outer tube member; conducting wires connected to one or more of the electrodes and disposed in the lumen, the conducting wires each having a coating; and a wire having a distal end portion fixed to a distal end portion of the outer tube member. A connection point between one of the electrodes and a conducting wire among the conducting wires and a connection point between another one of the electrodes and a conducting wire among the conducting wires are at different locations in a circumferential direction of the outer tube member. The conducting wire connected to the one of the electrodes and the conducting wire connected to the another one of the electrodes are disposed in the same lumen of the outer tube member. Accordingly, insulation property between the conducting wires to be subjected to application of voltages different from each other in polarity can be improved.

It is preferable that the above-described catheter further includes an inner tube member disposed in the lumen, the wire is disposed inside the inner tube member, and the inner tube member and the wire are disposed in the lumen in which the conducting wires are disposed. Accordingly, the wire and the conducting wires are disposed in different spaces in the lumen, whereby the insulation properties of the conducting wires can be prevented from deteriorating owing to contact between the wire and the conducting wires.

It is preferable that, in the above-described catheter, a distal side of the outer tube member bendable to one side by moving the wire in an axial direction, and in a cross section perpendicular to the axial direction of the outer tube member at a bending portion of the outer tube member, at least one position of at least one of the conducting wires is disposed on the one side among the one side and another side opposite to the one side of the outer tube member. Accordingly, a load is less likely to be applied to the conducting wires when the outer tube member is bent, whereby damage to the coatings of the conducting wires and breakage of the conducting wires can be prevented. Therefore, the insulation properties of the conducting wires can be maintained.

It is preferable that, in the above-described catheter, the conducting wire connected to the one of the electrodes and the conducting wire connected to the another one of the electrodes are at different locations in the circumferential direction of the outer tube member. Accordingly, the insulation properties of the conducting wires can be prevented from deteriorating owing to contact between the conducting wires.

It is preferable that, in the above-described catheter, the inner tube member has a protective member disposed at a radially outward of the inner tube member. In addition, the protective member of the inner tube member is preferably formed from an insulating material different from an insulating material of the coating of each of the conducting wire. Owing to these features, the insulation properties of the conducting wires can be prevented from deteriorating owing to contact between the inner tube member and the conducting wires.

It is preferable that, in the above-described catheter, the protective member of the inner tube member is formed from a polyolefin-based resin. In addition, the coating of each of the conducting wire is preferably formed from a fluorine-based resin. Owing to these features, the insulation properties of the conducting wires can be prevented from deteriorating owing to contact between the inner tube member and the conducting wires.

It is preferable that, in the above-described catheter, a thickness of the coating of each of the conducting wire is not smaller than 20 µm and not larger than 50 µm. Accordingly, the coating of the conducting wire becomes less likely to fall off. Furthermore, the conducting wires can be prevented from coming into contact with each other in the lumen by the conducting wires becoming thick more than necessary.

It is preferable that the above-described catheter further includes an elastic member having a distal end portion fixed to the distal end portion of the outer tube member and having a proximal end portion fixed to the inner tube member. Accordingly, it is possible to finely adjust the extent to which the distal side of the outer tube member is to be bent by moving the wire in the axial direction.

It is preferable that the above-described catheter further includes a tubular member provided on a proximal side relative to the distal end portion of the wire, and the wire and the elastic member are disposed in an inner cavity of the tubular member. Accordingly, the coatings of the conducting wires can be prevented from being damaged by the conducting wires coming into contact with another object such as the wire disposed in the lumen of the outer tube member.

It is preferable that, in the above-described catheter, a proximal end portion of the tubular member is on a distal side relative to a distal end portion of the protective member of the inner tube member, a distal end of the protective member of the inner tube member and a proximal end of the tubular member are apart from each other, and a distal end portion of the inner tube member is fixed to an inside of the lumen of the outer tube member. Accordingly, the stiffness of a portion, of the outer tube member, to which the distal end portion of the inner tube member is fixed is increased, and the portion having an increased stiffness can be set as an origin from which the outer tube member is to be bent. Therefore, the manner of the bending of the outer tube member becomes easy to adjust.

It is preferable that, in the above-described catheter, a proximal end portion of the inner tube member is fixed to an inside of the handle. Accordingly, when a load such as a twist is applied to the outer tube member, the load is less likely to be transmitted to the conducting wires, whereby insulation property can be prevented from deteriorating owing to damage to the coatings of the conducting wires, or the like.

It is preferable that, in the above-described catheter, the inner tube member is a coil or a pipe. Accordingly, it is possible to impart an appropriate flexibility while improving the rigidity of the outer tube member. Therefore, insertion of the catheter into a blood vessel is facilitated, and the catheter is easily inserted even into a curvy blood vessel.

A manufacturing method for a catheter according to the embodiment of the present invention is a manufacturing method for a catheter including: an outer tube member having a lumen extending in a longitudinal direction; a handle provided on a proximal side of the outer tube member; a plurality of electrodes provided on a distal side of the outer tube member; conducting wires connected to one or more of the electrodes and disposed in the lumen and in the handle, the conducting wires each having a coating; an inner tube member disposed in the lumen; and a wire having a proximal end portion disposed in an inner cavity of the handle, and having a distal end portion fixed to a distal end portion of the outer tube member. A connection point between one of the electrodes and a conducting wire among the conducting wires and a connection point between another one of the electrodes and a conducting wire among the conducting wires are at different locations in a circumferential direction of the outer tube member. The conducting wire connected to the one of the electrodes and the conducting wire connected to the another one of the electrodes are disposed in the same lumen of the outer tube member. The manufacturing method includes: a first step of disposing the conducting wires in the outer tube member; and a second step of disposing at least one of the inner tube member or the wire in the outer tube member. The second step is performed after the first step. Accordingly, each conducting wire, and the inner tube member and the wire, can be made less likely to come into contact with each other.

As described above, the catheter of the present invention includes: an outer tube member having a lumen extending in a longitudinal direction; a handle provided on a proximal side of the outer tube member; a plurality of electrodes provided on the outer tube member; conducting wires connected to one or more of the electrodes and disposed in the lumen, the conducting wires each having a coating; and a wire having a distal end portion fixed to a distal end portion of the outer tube member. A connection point between one of the electrodes and a conducting wire among the conducting wires and a connection point between another one of the electrodes and a conducting wire among the conducting wires are at different locations in a circumferential direction of the outer tube member. The conducting wire connected to the one of the electrodes and the conducting wire connected to the another one of the electrodes are disposed in the same lumen of the outer tube member. Owing to this configuration, the space through which the conducting wires and the like pass is wide in the inner cavity of the outer tube member, and thus multi-polarization of the catheter and reduction in the diameter thereof can be achieved, and bending of the distal end portion of the catheter can be finely controlled. In addition, even though the conducting wires are disposed in the same lumen of the outer tube member, the insulation properties of the conducting wires can be sufficiently ensured.

The present application claims the benefit of priority based on Japanese patent application number 2018-19459 filed on Feb. 6, 2018. The entire content of the specification of Japanese patent application number 2018-19459 filed on Feb. 6, 2018 is incorporated herein by reference.

DESCRIPTION OF REFERENCE SIGNS

1: catheter
2: lumen
3: outer tube member
4: handle
5: electrode
5a: one-side electrode
5b: other-side electrode
6: conducting wire
6a: conducting wire connected to one-side electrode
6b: conducting wire connected to other-side electrode
7: wire
8a: connection point between one-side electrode and conducting wire
8b: connection point between other-side electrode and conducting wire
9: distal tip
10: hole
11: bending portion of outer tube member
12: inner tube member
13: protective member
14: elastic member
15: tubular member
S1: straight line passing center point of smallest circle circumscribing outer tube member and connection point between one-side electrode and conducting wire
S2: straight line passing center point of smallest circle circumscribing outer tube member and connection point between other-side electrode and conducting wire
θ1: angle between straight line S1 and straight line S2

The invention claimed is:

1. A catheter comprising:
an outer tube member having a lumen extending in a longitudinal direction;
a handle provided on a proximal side of the outer tube member;
a plurality of ring-shaped electrodes provided on the outer tube member, the plurality of ring-shaped electrodes including a negative electrode and a positive electrode;
conducting wires connected to the plurality of ring-shaped electrodes and disposed in the lumen, the conducting wires each having a coating;
an operating wire having a distal end portion fixed to a distal end portion of the outer tube member;
an inner tube member disposed in the lumen;
an elastic member having a distal end portion fixed to the distal end portion of the outer tube member and having a proximal end portion fixed to the inner tube member; and
a tubular member provided on a proximal side relative to the distal end portion of the operating wire, wherein
a first connection point, at which one of said conducting wires is connected to one of the plurality of ring-shaped electrodes, and a second connection point, at which another conducting wire of said conducting wires is connected to another of the plurality of ring-shaped electrodes, are disposed at different locations in a circumferential direction of the outer tube member,
said one of the conducting wires connected to the first connecting point and said another conducting wire of the conducting wires connected to the second connecting point are disposed together in the lumen of the outer tube member,
the operating wire is disposed inside the inner tube member,
the inner tube member and the of wire are disposed in the lumen in which the conducting wires are disposed,
the inner tube member has a protective member disposed on a radially outward position of the inner tube member, and
the operating wire and the elastic member are disposed in an inner cavity of the tubular member.

2. The catheter according to claim 1, wherein
a distal side of the outer tube member is bendable to one side by moving the operating wire in an axial direction, and
in a cross section perpendicular to the axial direction of the outer tube member at a bending portion of the outer tube member, at least one of the conducting wires is disposed at a side same as the one side to which the distal side of the outer tube member is bendable or another side opposite to the one side of the outer tube member.

3. The catheter according to claim 1, wherein the protective member of the inner tube member is formed from an insulating material different from an insulating material of the coating of each of the conducting wires.

4. The catheter according to claim 1, wherein protective member of the inner tube member is formed from a polyolefin-based resin.

5. The catheter according to claim 1, wherein the coating of each of the conducting wires is formed from a fluorine-based resin.

6. The catheter according to claim 1, wherein a thickness of the coating of each of the conducting wires is not smaller than 20 μm and not larger than 50 μm.

7. The catheter according to claim 1, wherein
a proximal end portion of the tubular member is on a distal side relative to a distal end portion of the protective member of the inner tube member, and
a distal end portion of the inner tube member is fixed an inside of the outer tube member.

8. The catheter according to claim 1, wherein the inner tube member is fixed to an inside of the handle.

9. The catheter according to claim 1, wherein the inner tube member is a coil or a pipe.

10. A manufacturing method for a catheter comprising
an outer tube member having a lumen extending in a longitudinal direction,
a handle provided on a proximal side of the outer tube member,
a plurality of ring-shaped electrodes provided on a distal side of the outer tube member, the plurality of ring-shaped electrodes including a negative electrode and a positive electrode,
conducting wires connected to the plurality of ring-shaped electrodes and disposed in the lumen and in the handle, the conducting wires each having a coating,
an inner tube member disposed in the lumen,
an operating wire having a proximal end portion disposed in an inner cavity of the handle, and having a distal end portion fixed to a distal end portion of the outer tube member,
an elastic member having a distal end portion fixed to the distal end portion of the outer tube member and having a proximal end portion fixed to the inner tube member, and
a tubular member provided on a proximal side relative to the distal end portion of the operating wire,
a first connection point, at which one of said conducting wires is connected to one of the plurality of ring-shaped electrodes, and a second connection point, at which another conducting wire of said conducting wires is connected to another of the plurality of ring-shaped electrodes, being disposed at different locations in a circumferential direction of the outer tube member,
said one of the conducting wires connected to the first connecting point and said another conducting wire of the conducting wires connected to the second connecting point being disposed together in the lumen of the outer tube member, wherein
the operating wire is disposed inside the inner tube member,
the inner tube member and the operating wire are disposed in the lumen in which the conducting wires are disposed,
the inner tube member has a protective member disposed on a radially outward position of the inner tube member, and
the operating wire and the elastic member are disposed in an inner cavity of the tubular member,
the manufacturing method comprising:
a first step of disposing the conducting wires in the outer tube member; and
a second step of disposing at least one of the inner tube member and the operating wire in the outer tube member, wherein
the second step is performed after the first step.

* * * * *